US00PP37796P2

(12) United States Plant Patent
Sato

(10) Patent No.: US PP37,796 P2
(45) Date of Patent: Oct. 20, 2026

(54) ***BIDENS* PLANT NAMED 'SUNBIDEV 10'**

(50) Latin Name: *Bidens ferulifolia*
Varietal Denomination: SUNBIDEV 10

(71) Applicant: Kazunori Sato, Tokyo (JP)

(72) Inventor: Kazunori Sato, Tokyo (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/559,717

(22) Filed: Mar. 6, 2026

(51) Int. Cl.
*A01H 6/14* (2018.01)
*A01H 5/02* (2018.01)

(52) U.S. Cl.
USPC ..... Plt./410

(58) Field of Classification Search
USPC ..... Plt./410
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Bidens* plant named 'SUNBIDEV 10', characterized by its compact, upright to somewhat outwardly spreading and mounding plant habit; vigorous growth habit; freely branching habit; freely flowering habit; year-round flowering habit; large inflorescences with red and orange bi-colored ray florets; and tolerance to rain and low and high temperatures.

2 Drawing Sheets

Figure 1:
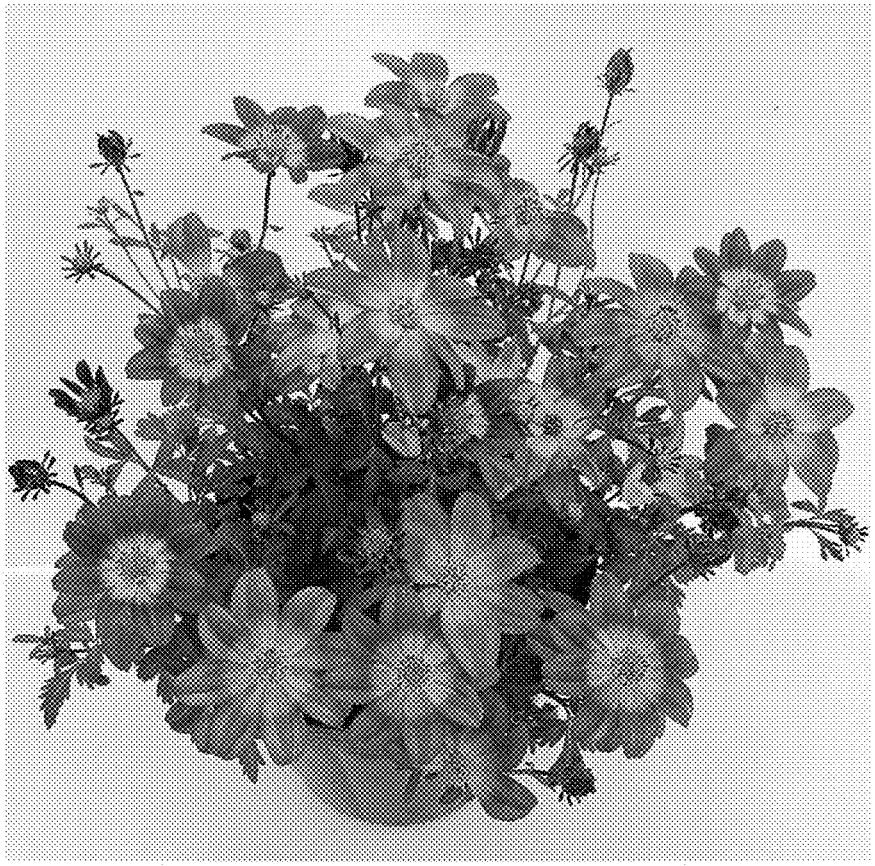

Botanical designation: *Bidens ferulifolia.*
Cultivar denomination: 'SUNBIDEV 10'.

BACKGROUND OF THE INVENTION

The present invention relates to a new and distinct cultivar of *Bidens* plant, botanically known as *Bidens ferulifolia* and hereinafter referred to by the name 'SUNBIDEV 10'.

The new *Bidens* plant is a product of a planned breeding program conducted by the Inventor in Fukaya, Saitama, Japan. The objective of the breeding program is to create new compact and mounding *Bidens* plants with year-round flowering habit and numerous inflorescences with red and orange-colored ray florets.

The new *Bidens* plant originated from a cross-pollination made by the Inventor in Fukaya, Saitama, Japan in April, 2019 of a proprietary selection of *Bidens ferulifolia* identified as code number 14-9-3, not patented, as the female, or seed parent with a proprietary selection of *Bidens ferulifolia* identified as code number 17-9-1, not patented, as the male, or pollen, parent. The new *Bidens* plant was discovered and selected by the Inventor as a single flowering plant from within the progeny of the stated cross-pollination in a controlled greenhouse environment in Fukaya, Saitama, Japan in March, 2020.

Asexual reproduction of the new *Bidens* plant by vegetative cuttings in a controlled environment in Fukaya, Saitama, Japan since December, 2020 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SUNBIDEV 10'. These characteristics in combination distinguish 'SUNBIDEV 10' as a new and distinct *Bidens* plant:

1. Compact, upright to somewhat outwardly spreading and mounding plant habit.
2. Vigorous growth habit.
3. Freely branching habit.
4. Freely flowering habit.
5. Year-round flowering habit.
6. Large inflorescences with red and orange bi-colored ray florets.
7. Tolerance to rain and low and high temperatures.

Plants of the new *Bidens* differ primarily from plants of the female parent selection in growth habit as plants of the new *Bidens* are more compact than plants of the female parent selection.

Plants of the new *Bidens* differ primarily from plants of the male parent selection in the following characteristics:

1. Plants of the new *Bidens* are more compact than plants of the male parent selection.
2. Inflorescences of plants of the new *Bidens* have more ray florets than inflorescences of plants of the male parent selection.

Plants of the new *Bidens* can be compared to plants of *Bidens ferulifolia* 'Sunbidevb 2', disclosed in U.S. Plant Pat. No. 27,703. In side-by-side comparisons, plants of the new *Bidens* differ primarily from plants of 'Sunbidevb 2' in the following characteristics:

1. Plants of the new *Bidens* are shorter and not as broad as plants of 'Sunbidevb 2'.
2. Plants of the new *Bidens* have shorter, broader and darker green-colored leaves than plants of 'Sunbidevb 2'.

3. Plants of the new *Bidens* have larger inflorescences than plants of 'Sunbidevb 2'.
4. Plants of the new *Bidens* have red and orange bicolored ray florets whereas plants of 'Sunbidevb 2' have yellow orange and bright orange red-colored ray florets.
5. Plants of the new *Bidens* have shorter peduncles than plants of 'Sunbidevb 2'.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph on the first sheet (FIG. 1) is a side perspective view of a typical flowering plant of 'SUNBIDEV 10' grown in a container.

Figure 2:
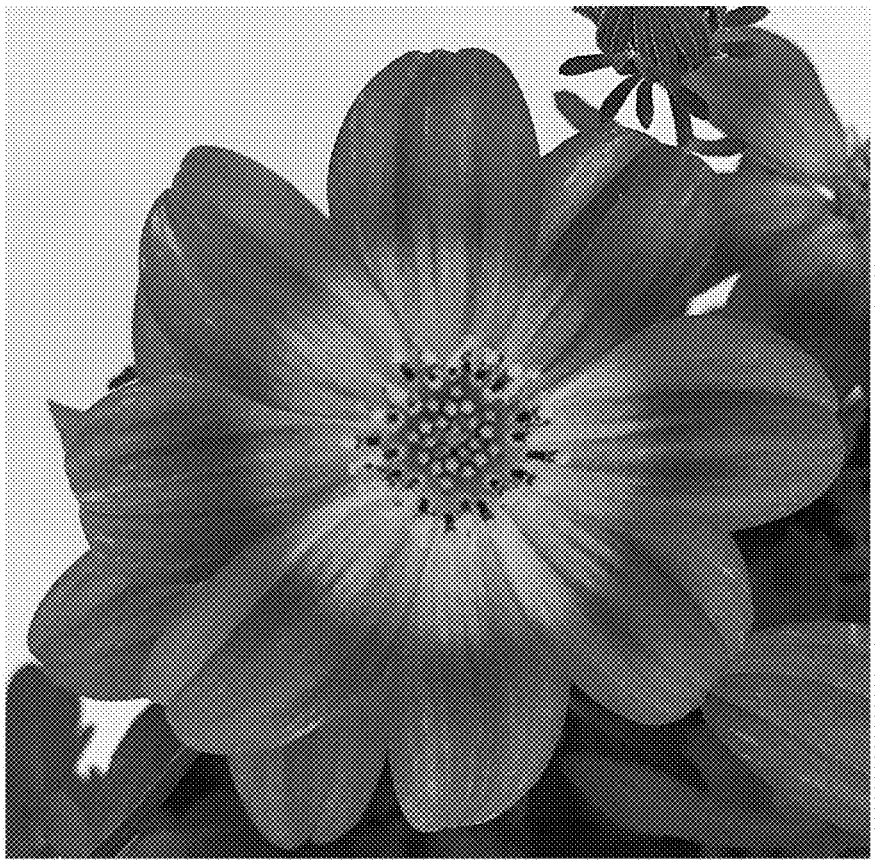

The photograph on the second sheet (FIG. 2) is a close-up view of typical inflorescences of 'SUNBIDEV 10'.

DETAILED BOTANICAL DESCRIPTION

The aforementioned photographs and following observations and measurements describe plants grown in 18-cm containers during the spring in an outdoor nursery in Higashiomi, Shiga, Japan and under cultural practices typical of commercial *Bidens* production. During the production of the plants, day temperatures ranged from 20° C. to 30° C. and night temperatures ranged from 10° C. to 20° C. Plants were three months old when the photographs and description were taken. In the following description, color references are made to The Royal Horticultural Society Colour Chart, 2015 Edition, except where general terms of ordinary dictionary significance are used.

Botanical classification: *Bidens ferulifolia* 'SUNBIDEV 10'.

Parentage:

*Female, or seed, parent*.—Proprietary selection of *Bidens ferulifolia* identified as code number 14-9-3, not patented.

*Male, or pollen, parent*.—Proprietary selection of *Bidens ferulifolia* identified as code number 17-9-1, not patented.

Propagation:

*Type*.—By vegetative cuttings.

*Time to initiate roots, summer*.—About seven days at temperatures ranging from 20° C. to 25° C.

*Time to initiate roots, winter*.—About ten days at temperatures ranging from 12° C. to 15° C.

*Time to produce a rooted young plant, summer*.—About ten days at temperatures ranging from 20° C. to 25° C.

*Time to produce a rooted young plant, winter*.—About two weeks at temperatures ranging from 12° C. to 15° C.

*Root description*.—Fibrous; typically white in color, actual color of the roots is dependent on substrate composition, water quality, fertilizers, substrate temperature and physiological age of roots.

*Rooting habit*.—Freely branching.

Plant description:

*Plant and growth habit*.—Compact, upright to somewhat outwardly spreading and mounding plant habit; vigorous growth habit.

*Branching habit*.—Freely branching habit with about five primary lateral branches with secondary lateral branches potentially forming at every node.

*Plant height*.—About 20 cm.

*Plant diameter or spread*.—About 23.4 cm.

*Lateral branches*.—Length: About 12.2 cm. Diameter: About 2 mm. Internode length: About 2.1 cm. Aspect: Upright to outwardly. Texture: Glabrous to sparsely pubescent. Color: Close to 145A.

Leaf description:

*Arrangement*.—Opposite, simple.

*Length*.—About 2.9 cm.

*Width*.—About 3.2 cm.

*Shape*.—Roughly deltoid; pinnatisect.

*Apex*.—Acute.

*Base*.—Truncate.

*Margin*.—Serrate.

*Texture, upper and lower surfaces*.—Smooth, glabrous.

*Venation pattern*.—Pinnate, reticulate.

*Color*.—Developing and fully developed leaves, upper surface: Close to 137B; venation, close to 137D. Developing and fully expanded leaves, lower surface: Close to 138B; venation, close to 138C.

*Petioles*.—Length: About 8 mm. Diameter: About 1 mm. Texture, upper and lower surfaces: Pubescent. Color, upper and lower surfaces: Close to 138C.

Inflorescence description:

*Appearance*.—Large single inflorescences with ray and disc florets forming acropetally on a receptacle; upright inflorescences positioned above and beyond the foliar plane on sturdy peduncles; inflorescences face mostly upright.

*Flowering habit*.—Freely flowering habit with about 31 fully opened inflorescences at one time and numerous inflorescences developing per plant.

*Fragrance*.—Fragrant; pleasant.

*Natural flowering season*.—Plants flower continuously year-round in Japan; early flowering habit, plants begin flowering about 60 days after planting rooted young plants.

*Inflorescence longevity*.—Individual inflorescences last about seven to ten days on the plant; inflorescences not persistent.

*Inflorescence buds*.—Height: About 1.35 cm. Diameter: About 1.65 cm. Shape: Ovoid. Color: Close to 173A.

*Inflorescence size*.—Diameter: About 3.9 cm. Depth (height): About 1 cm. Disc diameter: About 7.7 mm.

*Receptacles*.—Diameter: About 4.4 mm. Height: About 1.3 cm. Color: Close to 138B.

*Ray florets*.—Number of ray florets per inflorescence: About six to eight arranged in a single whorl. Length: About 2.1 cm. Width: About 1.2 cm. Shape: Elliptic. Apex: Acute. Base: Obtuse. Margin: Entire. Aspect: Mostly flat and horizontal. Texture, upper and lower surfaces: Smooth, glabrous. Color: When opening, upper surface: Close to 42A; towards the base, close to 26A and at the base, close to 13A. When opening, lower surface: Close to 34B; towards the base, close to 13B. Fully opened, upper surface: Close to 42B; towards the base, close to 26A. Fully opened, lower surface: Close to 34C; towards the base, close to 13B; venation, close to 151A.

*Disc florets*.—Number of disc florets per inflorescence: About 67.Shape: Tubular, elongated; apex, five-pointed. Length: About 5.7 mm. Diameter: Distally, about 1.4 mm; proximally, about 0.9 mm. Texture, inner and outer surfaces: Smooth, glabrous. Color, inner and outer surfaces: Close to 13A.

*Phyllaries*.—Quantity per inflorescence: About nine. Length: About 4.7 mm. Width: About 1.3 mm. Shape: Lanceolate. Apex: Acute. Base: Truncate, fused. Margin: Entire. Texture, upper and lower surfaces: Smooth, glabrous. Color, upper surface: Close to 137A. Color, lower surface: Close to 137B.

*Peduncles*.—Length, terminal peduncle: About 3.4 cm. Diameter: About 1.1 mm. Strength: Sturdy. Aspect: Upright to outwardly, inflorescences held above and beyond the foliar plane. Texture: Smooth, glabrous. Color: Close to 145A.

*Reproductive organs*.—Androecium: Present on disc florets only. Quantity per disc floret: Five. Filament length: About 2.3 mm. Filament color: Close to 145D. Anther shape: Lanceolate. Anther length: About 1.1 mm. Anther color: Close to N92A. Pollen amount: Moderate. Pollen color: Close to 12A. Gynoecium: Present on ray and disc florets. Pistil length: About 6 mm. Style color: Close to 150C. Stigma shape: Bifurcate. Stigma color: Close to 12A. Ovary color: Close to 145A.

*Seeds*.—To date, seed development has not been observed on plants of the new *Bidens*.

Pathogen & pest resistance: To date, plants of the new *Bidens* have not been shown to be resistant to pathogens and pests common to *Bidens* plants.

Garden performance: Plants of the new *Clematis* have exhibited good garden performance and to tolerate rain and temperatures ranging from 5° C. to 35° C.

It is claimed:

1. A new and distinct *Bidens* plant named 'SUNBIDEV 10' as herein illustrated and described.

* * * * *